United States Patent
Tesson et al.

(10) Patent No.: US 11,267,791 B2
(45) Date of Patent: Mar. 8, 2022

(54) HIGHLY STABLE CRYSTALLINE ELTROMBOPAG MONOETHANOLAMINE SALT FORM D1

(71) Applicant: F.I.S.—FABBRICA ITALIANA SINTETICI S.P.A., Montecchio Maggiore (IT)

(72) Inventors: Nicolas Tesson, Esplugues de Llobregat Barcelona (ES); Jordi De Mier Vinue, Esplugues de Llobregat Barcelona (ES); Paolo Stabile, Montecchio Maggiore (IT); Pierluigi Padovan, Montecchio Maggiore (IT); Matteo De Poli, Montecchio Maggiore (IT); Angelo Restelli, Montecchio Maggiore (IT)

(73) Assignee: F.I.S.—FABBRICA ITALIANA SINTETICI S.P.A., Montecchio Maggiore (IT)

( * ) Notice: Subject to any disclaimer, the term of this patent is extended or adjusted under 35 U.S.C. 154(b) by 0 days.

(21) Appl. No.: 17/263,642

(22) PCT Filed: Jul. 25, 2019

(86) PCT No.: PCT/EP2019/070077
§ 371 (c)(1),
(2) Date: Jan. 27, 2021

(87) PCT Pub. No.: WO2020/025449
PCT Pub. Date: Feb. 6, 2020

(65) Prior Publication Data
US 2021/0284611 A1    Sep. 16, 2021

(30) Foreign Application Priority Data
Aug. 2, 2018   (EP) .................................... 18187074

(51) Int. Cl.
*C07D 231/46*   (2006.01)

(52) U.S. Cl.
CPC ........ *C07D 231/46* (2013.01); *C07B 2200/13* (2013.01)

(58) Field of Classification Search
CPC .................................................. C07D 231/46
See application file for complete search history.

(56) References Cited

U.S. PATENT DOCUMENTS 8,372,822 B2    2/2013   Leksic et al.

FOREIGN PATENT DOCUMENTS

| WO | 0189457    A2 | 11/2001 |
| WO | 03098992    A2 | 12/2003 |
| WO | 2010114943 A1 | 10/2010 |

OTHER PUBLICATIONS

International Search Report and Written Opinion for Corresponding International Application No. PCT/EP2019/070077 (8 Pages) (dated Oct. 1, 2019).

*Primary Examiner* — Shawquia Jackson
(74) *Attorney, Agent, or Firm* — Lucas & Mercanti, LLP (57) ABSTRACT

Object of the present invention is a highly stable crystalline form of Eltrombopag (ETP) monoethanolamine salt, named Form D1, having the highest thermodynamically stability with excellent non-hygroscopicity, and particularly well suitable for pharmaceutical purposes, with related process.

14 Claims, 4 Drawing Sheets

HIGHLY STABLE CRYSTALLINE ELTROMBOPAG MONOETHANOLAMINE SALT FORM D1

CROSS-REFERENCE TO RELATED APPLICATIONS

This application is a 371 of PCT/EP2019/070077, filed Jul. 25, 2019, which claims the benefit of European Patent Application No. 18187074.2, filed Aug. 2, 2018.

TECHNICAL FIELD

The present invention refers to a process for a highly stable crystalline Eltrombopag monoethanolamine salt form D1, which is a solid form particularly stable and well suitable for pharmaceutical purposes.

BACKGROUND ART

Eltrombopag (abbreviate with the acronym ETP) is a small molecule, non-peptide thrombopoitin (TPO) receptor agonist that stimulates the proliferation and differentiation of megakaryocytes.

ETP has the following chemical formula (II):

(II)

and has chemical name 3'-{(2Z)-2-[1-(3,4-dimethylphenyl)-3-methyl-5-oxo-1,5-dihydro-4H-pyrazol-4-ylidene]-hydrazino}-2'-hydroxy-3-biphenyl carboxylic acid or 3'-{N'-[1-(3,4-dimethylphenyl)-3-methyl-5-oxo-1,5-dihydropyrazol-4-ylidene] hydrazino}-2'-hydroxybiphenyl-3-carboxylic acid.

This molecule is an active pharmaceutical ingredient, which is known in the market with the commercial name Promacta® in the USA and Revolade® in most countries outside the USA.

Specifically, ETP is used to treat adults and children one year of age and older with low blood platelet counts due to chronic immune (idiopathic) thrombocytopenia (ITP), when other medicines to treat ITP or surgery to remove the spleen have not worked well enough.

Eltrombopag is commercialized in pharmaceutical compositions comprising this active pharmaceutical ingredient in form of Eltrombopag olamine or ETP olamine, i.e. a salt of ETP with ethanolamine in 1:2 ratio, also called Eltrombopag bisethanolamine salt of formula (III):

(III)

having molecular weight 564.65.

Eltrombopag olamine is supplied for oral administration in two strengths: 25 mg and 50 mg film-coated tablets.

This salt is a red/brown crystalline solid, sparingly soluble in water and non-hygroscopic. The molecule does not contain asymmetric centres although it exists as the Z-isomer in solution and the solid state. It is thermally stable up to about 125° C. At higher temperature, an endothermic reaction associated with its degradation occurs, as reported in Australian and EU assessment/Regulatory report.

A crystalline form of the above mentioned disalt is claimed by the originator in WO03098992, and other polymorphs of ETP olamine (example Form I, II, III, V and XVI) are disclosed in WO 2010/114943.

Moreover, an alternative to commercial ETP bisethanolamine salt is ETP monoethanolamine salt, which is used to prepare pharmaceutical formulation according to WO 2010/114943.

In particular, two crystalline Eltrombopag (ETP) monoethanolamine salt forms, i.e. ETP monoethanolamine salt Form H and ETP monoethanolamine salt Form E are described in WO 2010/114943.

Specifically, the paragraphs [00174] and [00175] of WO 2010/114943 disclose the XPRD peaks of ETP monoethanolamine salt form H, having characteristic peaks 2-Theta values (2θ) at: 4.9, 6.9, 15.1 and 23.0° 2θ±0.2°, and the process for preparing said Form H by crystallization of ETP bisethanolamine salt in 1-butanol or 1-pentanol, as shown in the example 37 and 38.

Moreover, said WO 2010/114943 describes ETP monoethanolamine salt form E, at paragraphs [00176] and [00177], with its XPRD characteristic peaks 2-Theta values (2θ) at: 10.5, 13.4, 19.5 and 21.8° 2θ±0.2°, and the process for preparing it in 2,2,2-trifluoroethanol, shown in the example 39.

Both processes for the preparation of the above two different ETP monoethanolamine salt forms, i.e. Form H and Form E, are carried out starting from ETP bisethanolamine salt.

SUMMARY OF INVENTION

The problem addressed by the present invention is therefore that of providing a better crystalline form of Eltrombopag (ETP) monoethanolamine salt, more thermodynamically stable, and process thereof, which allows to get a better product compared to those of the prior art.

This problem is solved by the crystalline Eltrombopag (ETP) monoethanolamine salt form D1, having the highest thermodynamic stability (see the lowest solubility in water, and the highest value of DSC onset and DSC peak), well suitable for pharmaceutical purposes.

The crystalline Eltrombopag (ETP) monoethanolamine salt form D1 is prepared by a process that starts from Eltrombopag free acid, as outlined in the annexed claims, whose definitions are integral part of the present description.

Further features and advantages of the process according to the invention will result from the description hereafter reported of examples of realization of the invention, provided as an indication and not as a limitation of the invention.

DESCRIPTION OF EMBODIMENTS

Object of the present invention is a crystalline Eltrombopag monoethanolamine salt Form D1 of formula (I):

(I)

having one of the following characteristic peaks of X-ray powder diffraction pattern expressed in 2-Theta values (2θ) at: 7.6, 11.6 and 16.5, each peak ±0.2.

It has been indeed surprisingly found that the crystalline form of Eltrombopag monoethanolamine salt Form D1 is highly stable and well suitable to be employed for pharmaceutical purposes. Moreover, it has been surprising that the above mentioned crystalline form can be produced starting from Eltrombopag (free acid), in a solvent with the addition of ethanolamine, produces a form of Eltrombopag monoethanolamine salt, having characteristic peaks of X-ray powder diffraction pattern and specific value of DSC analysis, i.e. DSC onset and DSC peak. Specifically, the crystalline Eltrombopag monoethanolamine salt Form D1 of the present invention can be suitable in the preparation of pharmaceutical formulation.

Moreover, the present invention provides a different process to provide a crystalline Eltrombopag monoethanolamine salt, compared to the above mentioned prior art, wherein ETP monoethanolamine salt forms are produced starting from ETP bisethanolamine salt.

Moreover, it has been observed that said ETP monoethanolamine salt Form D1 has a value of DSC onset and DSC peak, measured by DSC analysis, higher than other ETP monoethanolamine salt forms. This characteristic is an important evidence of the stability of the product.

Another very important advantage of the product of the present invention is that said ETP monoethanolamine salt Form D1 is more and higher stable than other ETP monoethanolamine salt forms, according to ICH guideline conditions, as better described in the following invention and in the experimental part. This characteristic/result of stability is important in the pharmaceutical composition, since it guarantees efficacy and safety.

Further aspect of the product of the present invention is that, Eltrombopag monoethanolamine salt Form D1 can be prepared heating at specific temperature Eltrombopag monoethanolamine salt Form H, whose preparation is disclosed in WO 2010/114943, as the starting material. Indeed, at defined temperature, ETP monoethanolamine salt Form H converts to ETP monoethanolamine salt Form D1, as it can be seen comparing FIG. 2 with FIG. 3.

The latest ETP monoethanolamine salt Form D1, as above described, is more stable than ETP monoethanolamine salt Form H, as reported in the present invention.

Finally, the product of the present invention, ETP monoethanolamine salt Form D1, being more stable under ICH guideline and having a high DSC onset, it can be a good alternative to other ETP monoethanolamine salt forms (i.e. ETP monoethanolamine salt Form H and ETP monoethanolamine salt Form E) or to ETP olamine in the preparation of pharmaceutical composition.

The crystalline Eltrombopag (ETP) monoethanolamine salt Form D1 of formula (I) of the present invention has one of the following characteristic peaks of X-ray powder diffraction pattern expressed in 2-Theta values (2θ) at: 7.6, 11.6 and 16.5, each peak ±0.2.

According to a preferred embodiment of the present invention, said crystalline ETP monoethanolamine salt Form D1 of formula (I) of the present invention has one of the following characteristic peaks of X-ray powder diffraction pattern expressed in 2-Theta values (2θ) at: 7.6, 11.6 and 16.5, each peak ±0.1.

According to further preferred embodiment of the present invention, the crystalline ETP monoethanolamine salt Form D1 of formula (I) has two or three of the following characteristic peaks of X-ray powder diffraction pattern expressed in 2-Theta values (2θ) at: 7.6, 11.6 and 16.5, each peak ±0.2; preferably each peak ±0.1.

According to a more preferred embodiment of the present invention, the crystalline ETP monoethanolamine salt Form D1 of formula (I) has characteristic peaks of X-ray powder diffraction pattern expressed in 2-Theta values (2θ) at: 7.6, 10.5, 11.6, 16.5 and 19.9, each peak ±0.2; preferably each peak ±0.1.

According to a preferred embodiment of the present invention, the crystalline ETP monoethanolamine salt Form D1 of formula (I) has characteristic peaks of X-ray powder diffraction pattern expressed in 2-Theta values (2θ) at: 5.3, 7.6 and 8.5, each peak ±0.2; preferably each peak ±0.1.

Specifically, the beforehand characteristic peaks of ETP monoethanolamine salt Form D1 of formula (I), i.e. 5.3, 7.6 and 8.5, each peak ±0.2, have an higher intensity value, as reported in the Table 1.

According to a particularly preferred embodiment of the present invention, the crystalline ETP monoethanolamine salt Form D1 of formula (I) has characteristic peaks of X-ray powder diffraction pattern expressed in 2-Theta values (2θ) at: 5.3, 7.6, 8.5, 11.6, 13.6 and 16.5, each peak ±0.2; preferably each peak ±0.1.

Figure 1:
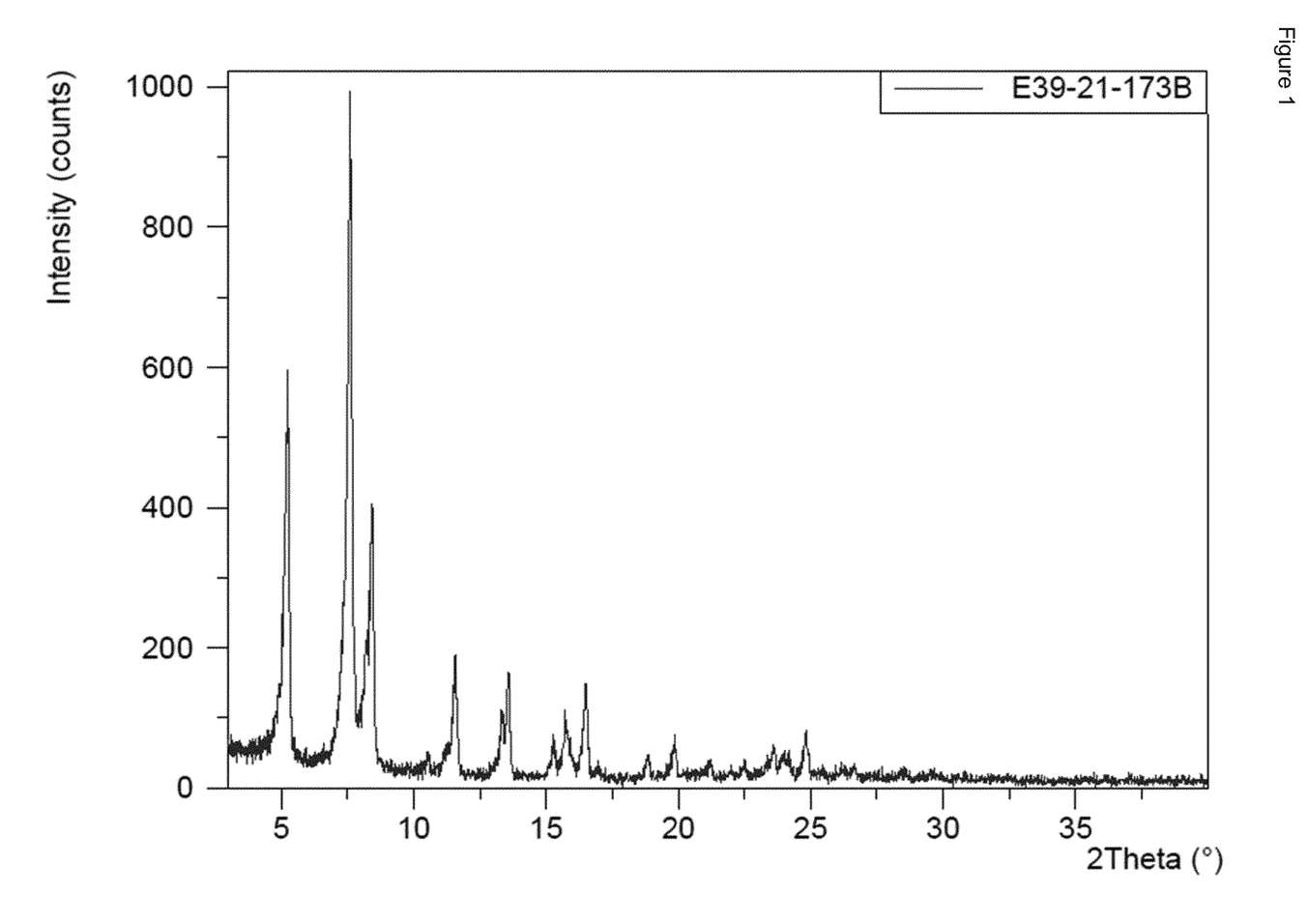
FIG. 1 shows the powder x-ray diffraction pattern of Eltrombopag monoethanolamine salt form D1 of formula (I), the product of the present invention.

Moreover, the list of the value of the peaks of X-powder diffraction ray pattern expressed in 2-Theta values (2θ) of the crystalline ETP monoethanolamine salt Form D1 of formula (I) is following reported in Table 1, and shown in FIG. 1:

TABLE 1

| Pos. [°2θ] | d-spacing [Å] | Rel. Int. [%] |
|---|---|---|
| 5.3 | 16.8 | 56 |
| 7.6 | 11.6 | 100 |
| 8.5 | 10.5 | 36 |
| 10.5 | 8.4 | 2 |
| 11.6 | 7.6 | 17 |
| 13.3 | 6.6 | 9 |
| 13.6 | 6.5 | 16 |
| 15.3 | 5.8 | 5 |
| 15.7 | 5.6 | 9 |
| 16.5 | 5.4 | 14 |
| 18.9 | 4.7 | 3 |
| 19.9 | 4.5 | 4 |
| 21.2 | 4.2 | 2 |
| 22.5 | 4.0 | 2 |
| 23.6 | 3.8 | 4 |
| 24.8 | 3.6 | 7 |

According to another preferred embodiment of the present invention, the crystalline Eltrombopag monoethanolamine salt Form D1 of formula (I) has DSC onset comprised in the range from 234° C. to 236° C. and/or DSC peak in the range from 238° C. to 240° C.

Specifically, the value of DSC onset is recorded as measured by DSC.

The DSC onset corresponds to the melting point value.

The DSC method is better described in the experimental part.

According to more preferred embodiment of the present invention, the crystalline Eltrombopag monoethanolamine salt Form D1 has onset 235° C. as measured by DSC.

According to more preferred embodiment of the present invention, the crystalline Eltrombopag monoethanolamine salt Form D1 has peak at about 239° C. as measured by DSC According to more preferred embodiment of the present invention, Eltrombopag monoethanolamine salt Form D1 has onset at about 235° C. and peak at about 239° C. both as measured by DSC.

Figure 2:
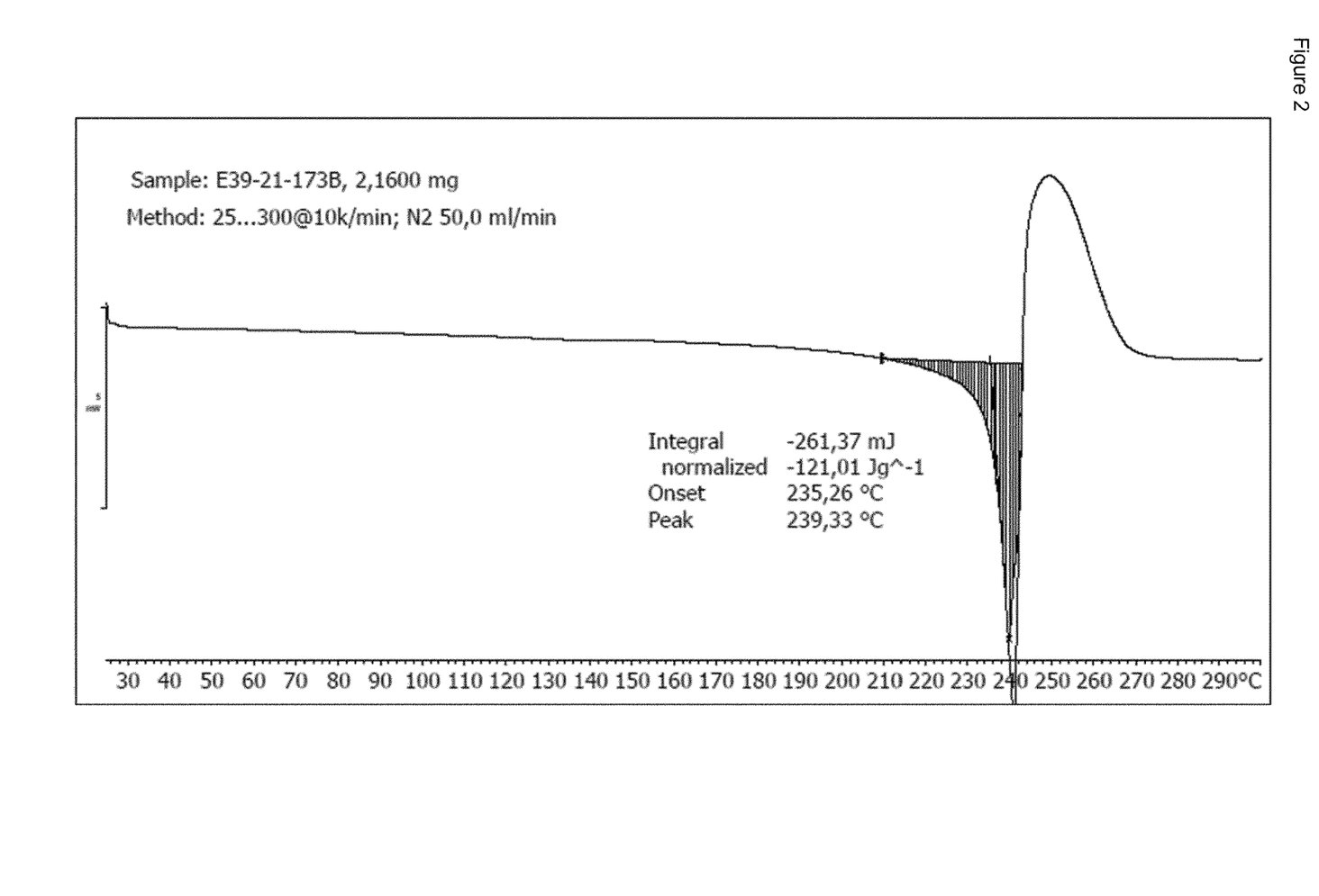
FIG. 2 shows the DSC curve of Eltrombopag monoethanolamine salt form D1 of formula (I), the product of the present invention.

Specifically, DSC analysis shows one endothermic event with an onset at 235° C. and a peak at 239° C., the value of onset corresponds to the melting point of ETP monoethanolamine salt Form D1, followed by large event due to a degradation event (see FIG. 2).

Figure 3:
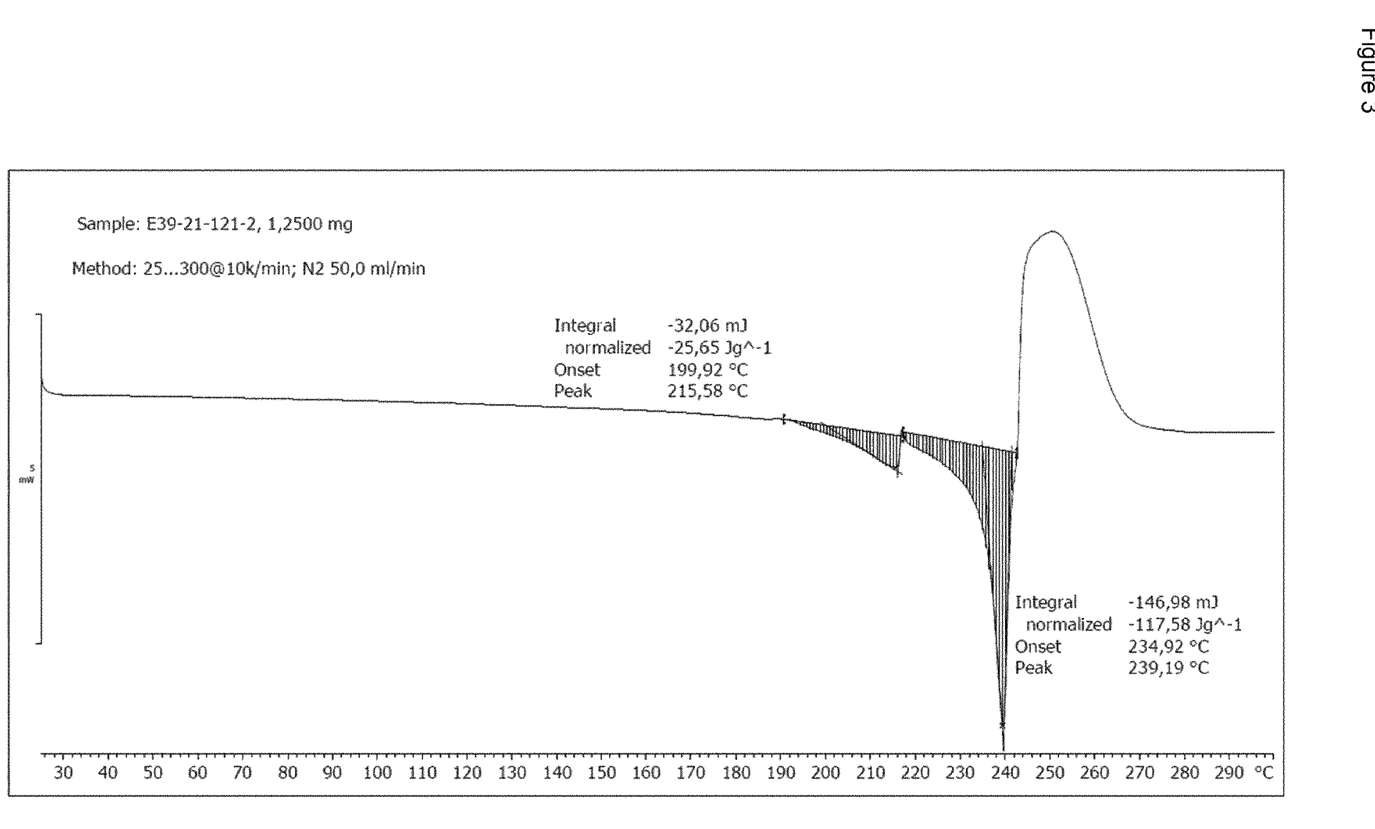
FIG. 3 shows the DSC curve of Eltrombopag monoethanolamine salt form H.

Moreover, the above mentioned DSC analysis of the crystalline ETP monoethanolamine salt Form D1 shows a linear curve having only one onset and one peak, that is an evidence of the own better stability compared with DSC analysis of Eltrombopag monoethanolamine salt Form H, wherein there are two peaks, as shown in FIG. 3.

Specifically, ETP monoethanolamine salt Form H, as disclosed in WO 2010/114943, has the characteristic peaks of X-ray powder diffraction pattern expressed in 2-Theta values (2θ) at: 4.9, 6.9, 15.1 and 23.0° 2θ±0.2°.

In particular, the DSC analysis of the crystalline ETP monoethanolamine salt Form H shows onset at about 199° C., i.e. melting point as measured by DSC, and peak at 215° C., moreover the same DSC analysis shows a second curve having an onset at about 234.9° C. and peak at 239.2° C.

The second curve of said DSC analysis corresponds exactly to the curve of the DSC analysis of the crystalline Eltrombopag monoethanolamine salt Form D1, as shown in FIG. 2.

Therefore, ETP monoethanolamine salt Form H converts to ETP monoethanolamine salt Form D1 during the first thermal melting.

Another aspect of the present invention is thus, the process for the preparation of the crystalline Eltrombopag monoethanolamine salt Form D1 of formula (I), above described:

(I)

comprising the following steps:
a) providing a suspension of Eltrombopag in a solvent,
b) heating the mixture of the step a) to give a solution,
c) adding to the solution of the step b) an amount of ethanolamine to give a suspension of Eltrombopag monoethanolamine salt Form D1 of formula (I):

(I)

in a solvent,
d) isolating Eltrombopag monoethanolamine salt Form D1 from the suspension of the step c).

In the step a), the suspension of Eltrombopag contains ETP free acid, i.e. Eltrombopag of formula (II):

(II)

suspended in a solvent.

Suspension means a solid material suspended in a solution, i.e. mixture of solid Eltrombopag is suspended in a solvent.

The starting material Eltrombopag free acid is commercially available, for example from Sigma-Aldrich Inc. (USA) with product code COM497515993 and product name Eltrombopag.

Moreover, the above mentioned starting material can be prepared, following the method disclosed in WO 01/89457, specifically, Example 3 describes its preparation.

According to preferred embodiment of the present invention, the solvent of the step a) is 1-pentanol or 1-butanol solvent.

According to preferred embodiment of the present invention, in the step a) ETP free acid is suspended in 1-pentanol or 1-butanol solvent.

According to preferred embodiment of the present invention, the heating of the step b) is carried out at reflux temperature.

Reflux temperature means the boiling point temperature of the solvent.

Specifically, in the step b), the mixture of the step a) is heated at temperature, wherein the solvent, i.e. 1-pentanol or 1-butanol, reaches the boiling point temperature, to give a solution.

Mixture means that two or more substances are combined such that each substance retains its own chemical identity.

Specifically, the mixture of the step a) contains Eltrombopag and 1-pentanol or 1-butanol solvent.

In the step b), the heating of the mixture of the step a) gives a solution.

Solution means to dissolve a solid compound in a solvent, for example the solution can be as an opalescent solution or a microsuspension or a suspension of little amount of solid material, typically an amount of insoluble material is less than 5% by weight of weight of the compound dissolved in a solvent. In the present invention, the solution is obtained from the dissolution of Eltrombopag in a solvent.

Specifically, in the present invention, Eltrombopag is dissolved in 1-pentanol or 1-butanol solvent.

Optionally, the resulting solution of the step b) could be stirred at about 80° C., to give a clear solution, before to proceed to the step c).

According to preferred embodiment of the present invention, the amount of ethanolamine of the step c) is comprised among 1.00 and 1.10 molar equivalent of ethanolamine, compared to ETP.

According to more preferred embodiment of the present invention, the amount of ethanolamine of the step c) is 1.00 molar equivalent of ethanolamine.

Molar equivalent means that the molar amount of a substance reacts with a molar amount of another substance in a given chemical reaction.

According to more preferred embodiment of the present invention, in the step c), the addition to the solution of the step b) an amount of ethanolamine, comprised among 1.00 and 1.10 molar equivalent of ethanolamine, to give a suspension of Eltrombopag monoethanolamine salt Form D1 of formula (I):

(I)

in a solvent, specifically in 1-pentanol or 1-butanol.

Specifically, when an amount of ethanolamine is added to the solution of the step b) gives a suspension of Eltrombopag monoethanolamine salt Form D1 of formula (I), more specifically a precipitation is observed to give a suspension.

According to a preferred embodiment of the process of the present invention, in the step d) Eltrombopag monoethanolamine salt Form D1 is isolated from the suspension of the step c).

Specifically, the isolation can be carried out cooling the suspension or isolating at high temperature, then the resulting solid is filtered, washed and finally dried, to obtain the crystalline Eltrombopag monoethanolamine salt Form D1, as described in the experimental part of the present invention.

Another aspect is thus, the process for the preparation of the crystalline Eltrombopag monoethanolamine salt Form D1 of formula (I), above described:

(I)

comprising the following steps:
A) heating solid Eltrombopag monoethanolamine salt Form H, having the characteristic peaks of X-ray powder diffraction pattern expressed in 2-Theta values (2θ) at: 4.9, 6.9, 15.1 and 23.0° 2θ±0.2°, at temperature comprised in the range from 200° C. to 210° C.,
B) maintaining at temperature of the step A) until the conversion of the product of the step A) to Eltrombopag monoethanolamine salt Form D1 of formula (I),
C) cooling the product of the step B).

Specifically, in the step A), Eltrombopag monoethanolamine salt Form H, having the characteristic peaks of X-ray powder diffraction pattern expressed in 2-Theta values (2θ) at: 4.9, 6.9, 15.1 and 23.0° 2θ±0.2°, is produced as described in WO2010/114943 at paragraph [00175] and in the example 37 and 38, by crystallization of ETP bisethanolamine salt in 1-butanol or 1-pentanol.

According to a preferred embodiment of the process of the present invention, the heating of the step A) is carried out at temperature comprised in the range from 200° C. to 205° C.

According to further preferred embodiment of the process of the present invention, the step A), and the following step, i.e. step B) and step C), are carried out without solvent.

According to a preferred embodiment of the process of the present invention, in the step B) temperature is maintained at the same range of the step A), i.e. comprised from 200° C. to 210° C., preferably from 200° C. to 205° C., until the conversion of the product of the step A) to Eltrombopag monoethanolamine salt Form D1 of formula (I).

Specifically, at said temperature ETP monoethanolamine salt Form H converts to ETP monoethanolamine salt Form D1. This completeness of the conversion can be verified by taking samples of obtained product and performing during the DSC analysis. (as explained in the example 4).

Then, in the step C), the product of the step B) is cooled, to give the crystalline ETP monoethanolamine salt Form D1, having one of the following characteristic peaks of X-ray powder diffraction pattern expressed in 2-Theta values (2θ) at: 7.6, 11.6 and 16.5, each peak ±0.2.

In particular, in the DSC analysis of ETP monoethanolamine salt Form H, its second curve corresponds to the DSC curve of ETP monoethanolamine salt Form D1, as beforehand better disclosed, and as seen in the FIGS. 2 and 3.

Another aspect is thus, a pharmaceutical composition comprises a crystalline Eltrombopag monoethanolamine salt Form D1 as above described, and one or more pharmaceutically acceptable excipients.

Indeed, said crystalline form of Eltrombopag monoethanolamine salt Form D1 is well stable and well suitable to be employed for pharmaceutical purposes, as show in the Example 8, which refers to stability study.

Moreover, a pharmaceutical composition can comprise a crystalline Eltrombopag monoethanolamine salt Form D1 in combination with a polymorphs of Eltrombopag bisethanolamine and one or more pharmaceutically acceptable excipients.

Pharmaceutical compositions have different dosage forms, which may include, for example, capsules, tablets, powders, suspensions or any other suitable dosage form. In such said dosage forms, Eltrombopag monoethanolamine salt Form D1 may be combined with one or more pharmaceutically acceptable excipients, carriers or diluents, such as, for example mannitol, silicic derivatives or sugar.

Another aspect of the present invention is thus, a crystalline Eltrombopag monoethanolamine salt Form D1 as above described or the pharmaceutical composition as beforehand discussed, for use as medicament.

Further aspect of the present invention is thus, a crystalline Eltrombopag monoethanolamine salt Form D1 as above described or the pharmaceutical composition as beforehand discussed, for the treatment of chronic immune thrombocytopenia.

According to a preferred embodiment, a crystalline Eltrombopag monoethanolamine salt Form D1 as above described or the pharmaceutical composition as beforehand discussed, can be used for the treatment of adults and children 1 years of age older with chronic immune thrombocytopenia.

Finally, considering that ETP monoethanolamine salt Form E is not stable, and therefore is discharged for pharmaceutical purposes (see example 5), the crystalline Eltrombopag monoethanolamine salt Form D1 has the lowest hygroscopicity at 95% RH, and moreover has the best thermodynamic stability (see the lowest solubility in water and the highest value of DSC onset and DSC peak), respect to other known ETP monoethanolamine salt Forms, therefore it is advantageously suitable for pharmaceutical purposes.

Experimental Section

The starting material Eltrombopag free acid can be prepared according to known prior art methods, for example, as described in in WO 01/89457 or can be purchased on the market (for example Sigma Aldrich).

The following table lists the abbreviations used:
ACN Acetonitrile
° C. Degree Centigrade or Degree Celsius
DSC Differential scanning calorimetry
EA Ethanolamine
EtOAc Ethyl acetate
eq. Equivalent
G Gramme
h Hour
HPLC High performance liquid chromatography
IPA Isopropyl alcohol
min minute
mg Milligramme
mL Millilitre
mmol Millimole
MTBE Methyl-tert-butyl ether or tert-butyl methyl ether
NMR nuclear magnetic resonance
RH relative humidity
rpm revolutions per minute
RT Room temperature
T Temperature
THF Tetrahydrofuran
V Volume
w/w Weight/weight
XPRD X-ray Powder Diffraction
μL Microlitre Example 1: Process for the Preparation of the Crystalline Eltrombopag Monoethanolamine Salt Form D1 of Formula (I)

In a round bottom flask (25 ml), ETP free acid (292 mg, 0.66 mmol) and 1-butanol (5.9 ml, 30 Vol) were heated to reflux. To the resulting red solution, was added ethanolamine (40 ml, 0.66 mmol, 1 eq.). The mixture turned dark and precipitation was observed. The suspension was allowed to cool down at RT and stirred for 15 h, then it was filtered and the resulting orange solid was washed with additional 1-butanol (2×1 ml). After drying at RT under vacuum, were obtained 294 mg (Y=85%) of the crystalline Eltrombopag monoethanolamine salt Form D1 of formula (I) were recovered according to XRPD analysis (shown FIG. 1).

Example 2: Process for the Preparation of the Crystalline Eltrombopag Monoethanolamine Salt Form D1 of Formula (I), Containing an Optional Stirring at the Step b)

(I)

In an assay tube, ETP free acid (74.3 mg, 0.17 mmol) and 1-pentanol (1.5 ml) were heated to reflux. Optionally, the resulting clear solution was stirred at 80° C. before adding ethanolamine (10 µl, 0.17 mmol). The crude mixture turned dark and a precipitate appeared.

Then the mixture was allowed to cool down at RT. Due to stirring issues, 1-pentanol (1 ml) was added to improve the stirring. After 30 min at RT, the crude was cooled to 0-5° C. with an ice-water bath for 45 min. The resulting orange solid was filtered and washed with additional 1-pentanol (2×0.5 ml). After drying for 12 h at RT under vacuum and for 6 h at 50° C. under vacuum, and obtained 55.3 mg (Y=65%) of the crystalline Eltrombopag monoethanolamine salt Form D1 was obtained according to XRPD analysis, which is equivalent to XRPD analysis of the FIG. 1.

Example 3: XPRD Diffractometer and Method for the Characterization of the Crystalline Eltrombopag Monoethanolamine Salt Form D1 of Formula (I), i.e. the Product of the Present Invention Diffraction measurements were performed at ambient conditions on a PANalytical X'Pert PRO 2 theta (2θ) diffractometer of 240 mm of radius in reflection geometry, equipped with Cu Kα radiation and a PIXcel detector, operated at 45 kV and 40 mA.

A sample of the crystalline Eltrombopag monoethanolamine salt Form D1 was mounted on a zero-background silicon holder and allowed to spin at 0.25 rev/s during the data collection. The measurement angular range was 3.0-40.0° (2θ) with a step size of 0.013°. The scanning speed was 0.0328°/s for routine analysis and 0.082°/s for characterization and final product analysis.

This analysis of XRPD diffractogram, as disclosed in the description part of the invention, and showed in FIG. 1.

In particular, the crystalline Eltrombopag monoethanolamine salt Form D1 of formula (I) has one of the following characteristic peaks of X-ray powder diffraction pattern expressed in 2-Theta values (2θ) at: 7.6, 11.6 and 16.5, each peak ±0.2.

Example 4: DSC

DSC analyses were recorded with a Mettler Toledo DSC2. Samples were weighed into a 40 µL aluminium crucible with a pinhole lid and heated at 10K/min from 25 to 300° C. under nitrogen (50 mL/min).

DSC Analysis of the Crystalline Eltrombopag Monoethanolamine Salt Form D1 of Formula (I):

An amount of sample of Eltrombopag monoethanolamine salt Form D1 were analysed by DSC.

Said DSC analysis shows one endothermic event with an onset at 235° C. that corresponds to the melting of ETP monoethanolamine salt Form D1 and a peak at 239° C., followed by a large exothermic event due to a degradation event (as shown in FIG. 2).

DSC Analysis of the Eltrombopag Monoethanolamine Salt Form H:

1.2500 mg of sample of Eltrombopag monoethanolamine salt Form H were analysed by DSC.

DSC analysis shows two endothermic events:
the first having an onset at about 199° C. and a peak at 215° C.
the second having an onset at about 234.9° C. and a peak at 239.2° C.

In particular, the first endothermic event, with an onset at about 199° C., corresponds to a polymorphic transition of ETP monoethanolamine salt Form H to another crystalline form, in particular at temperature between 200° C. to 210° C., ETP monoethanolamine salt Form H converts to Eltrombopag monoethanolamine salt Form D1, as provide by XPRD diffractogram and token a samples of the product. Following, the second endothermic event, with an onset at about 235° C., corresponds to the melting of the crystalline Eltrombopag monoethanolamine salt Form D1 (as shown in FIG. 2).

Example 5: Stability Study of Eltrombopag Monoethanolamine Salt Form E

The stability of Eltrombopag monoethanolamine salt Form E, whose preparation is described in background of the present invention, was carried out following two different conditions.

In the first ETP monoethanolamine salt Form E was exposed to atmospheric conditions for 1 day was unstable, and a new form very similar to Form II (ETP bisethanolamine salt) described in U.S. Pat. No. 8,372,822B2 was recovered according to XRPD analysis.

In the second ETP monoethanolamine salt Form E was exposed to ICH guideline accelerated conditions (40° C./75 RH %). Under these conditions, Form E converted partially to a new unknown form.

Results of stability study after 1 day of exposition:
1) Atmospheric conditions: Form II+one peak at 8.6° (2θ),
2) 40° C./75 RH %: partial conversion to a new form with a main peak at 8.6° (2θ).

Therefore, ETP monoethanolamine salt Form E is not stable under atmospheric or ICH guideline accelerated conditions for 1 day, and therefore not suitable for pharmaceutical purpose.

Example 6: Hygroscopicity Study of Various Crystalline Eltrombopag Monoethanolamine Salt Forms: ETP Monoethanolamine Salt Form D1, ETP Monoethanolamine Salt Form H, ETP Monoethanolamine Salt Form D, ETP Monoethanolamine Salt Form H2

Hygroscopicity study was determined by DVS (Dynamic Vapour Sorption) with a Q5000 TA instrument. This is a gravimetric technique that measures how much water is absorbed or desorbed by a sample at different relative humidity (RH). At each RH, the sample mass must be allowed to reach gravimetric equilibrium (or surpassed time limit) before progressing to the next humidity level. Sorption and desorption isotherms were performed at 25° C. over a range of 0-95% RH.

The samples gently milled were not previously dried but they were exposed to 0% RH until a stable weight was reached before starting the DVS cycle. This equilibration step allows possible adsorbed humidity to be eliminated.

DVS analyses were performed with ca. 10 mg of the 4 crystalline ETP monoethanolamine salt forms (Form D, Form H, Form D1 and Form H2) following the conditions described below:
weight equilibration at 25° C. under 0% RH,
increase to the higher RH % level when the weigh variation of the sample is inferior to 0.02% w/w after 10 min or after a time limit of 300 min.

Figure 4:
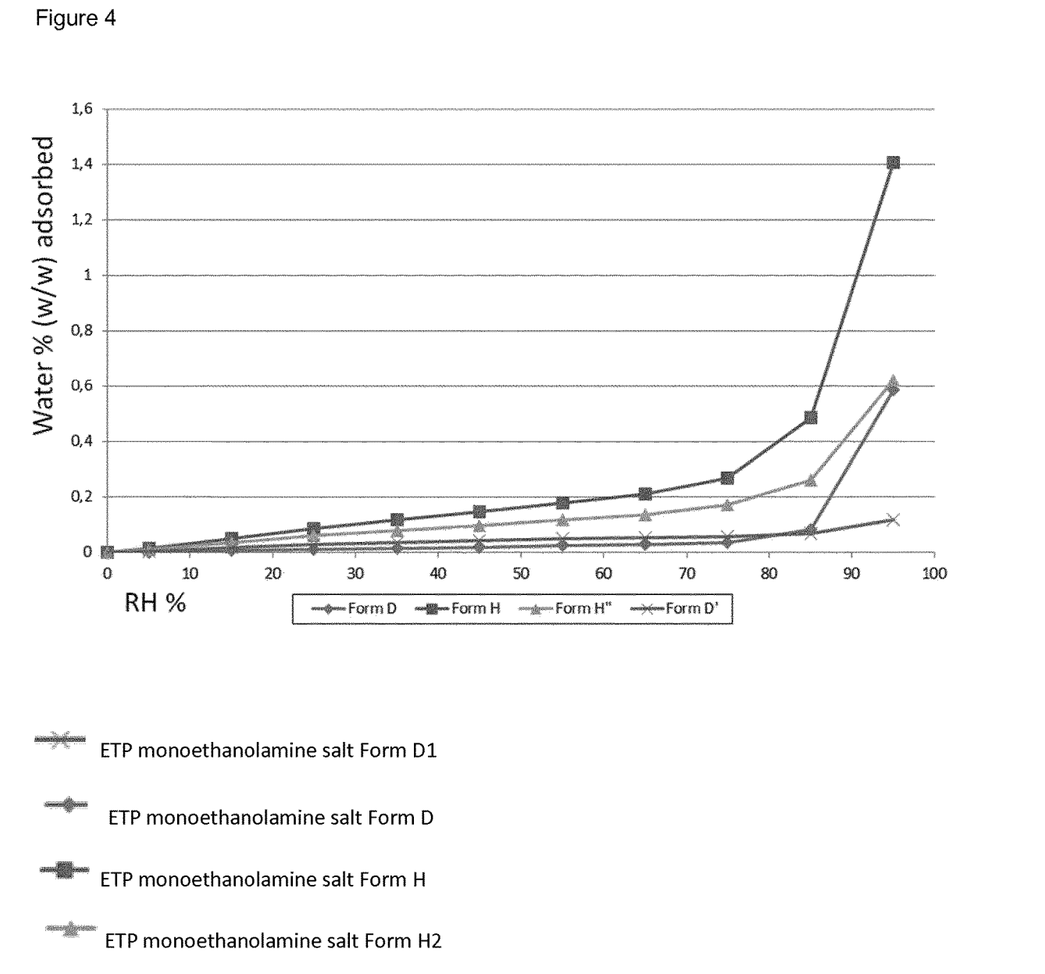
FIG. 4 shows the humidity adsorption curves of four ETP monoethanolamine salt forms, described in the example 6.

A graphic comparison of the humidity absorption profile of the 4 forms is shown on FIG. 4.

DVS analysis of the different monoethanolamine salts indicated that the water uptake increases progressively between 0 and 85% RH before increasing faster at 95% RH. However, the final water uptake remains low indicating that these forms are slightly hygroscopic (up to 1.4% w/w at 95% RH).

a. ETP monoethanolamine salt Form H is the most hygroscopic form, adsorbing up to 1.4% w/w of humidity at 95% RH.
b. ETP monoethanolamine salt Form H2, unknown in literature, is a form similar to ETP monoethanolamine salt Form H. Said ETP monoethanolamine salt Form H2 has a hygroscopicity similar to Form H up to 85% RH, but remained lower at 95% RH (0.6 vs 1.4 w/w).
c. ETP monoethanolamine salt Form D is not hygroscopic up to 85% RH.
d. ETP monoethanolamine salt Form D1 has the best non-hygroscopic behavior at 95% RH, less than 0.2% w/w at 95% RH (see FIG. 4).

The solids recovered after the DVS analysis cycle maintained their initial crystalline form according to XRPD (crystalline conversion did not occur).

Therefore, ETP monoethanolamine salt Form D1 shows a lower hygroscopitiy respect to Form H, previously described in the literature.

Therefore, ETP monoethanolamine salt Form D1 has a better hygroscopicity behaviour than all known ETP monoethanolamine salt Forms, and unknown Form, as Form H2.

Example 7: Water Solubility Study of Different Crystalline Eltrombopag Monoethanolamine Salt Forms: ETP Monoethanolamine Salt Form D1, ETP Monoethanolamine Salt Form H, ETP Monoethanolamine Salt Form D, ETP Monoethanolamine Salt Form H2

The relative solubility of the above mentioned 4 ETP monoethanolamine salt Forms was studied in water at RT. The validity of any solubility measurement requires that the crystalline form must remain stable with respect to any phase conversion taking place during the determination of the equilibrium solubility.

Preliminary Stability in Water

A preliminary test stability study in water at RT of 4 ETP monoethanolamine salt Forms was performed in order to observed possible crystalline transitions.

A sample of each crystalline form was slurried in water at RT and periodically analysed by XRPD (1, 3, 6 and 24 h) in order to detect possible crystalline transformation.

ETP monoethanolamine salt Form D1, Form H, Form D and Form H2 remained stable 24 h under these conditions. Then, their thermodynamic solubility can be determined.

Determination of Relative Thermodynamic Solubility in Water at RT by HPLC

Once confirmed that the different ETP monoethanolamine forms are stable under water, the thermodynamic solubility of these forms was evaluated.

As the solubility of these forms was very low in water, a suspension (10 mg in 1 mL of water) was performed in water at RT in order to afford a saturated solution. This suspension was stirred 24 h at RT in order to reach the equilibrium. Then, a sample was filtered and the resulting filtrate was analysed by HPLC by duplicate. The average peak area of ETP gave a relative value of the thermodynamic solubility of each form that can be compared with each other. The solids recovered after filtration were also analysed by XRPD to check that no crystalline phase transformation occurred during the slurring.

The following HPLC conditions were used to determine the relative solubility (due to their short analysis time and good response):
Column: C18 Zorbax Eclipse (XDB), 150×4.6 mm, 5 µm
Sample concentration: Saturated water solution of the ETP monoethanolamine salt
Mobile phase: ACN:MeOH:H2O (55:35:10) at pH=6.0+/−0.2
Temperature: 27° C.
Flow rate: 1 mL/min
UV detector wavelength: 230 nm
Injection: 5 µL
Run time: 10 min HPLC ETP peak area in each of the different forms analysed was measured in order to establish their relative solubility. The HPLC analyses were performed by duplicate for each ETP monoethanolamine salt. This solubility study was repeated twice in order to confirm the solubility values, as reported in the following Table 2).

TABLE 2

| Entry | Form | Solubility test #1 (area counts) | Solubility test #2 (area counts) | Intensity test average | Standard deviation |
|---|---|---|---|---|---|
| 1 | Form D1 | 2722 | 3100 | 2911 | 267 |
| 2 | Form H | 3963 | 5031 | 4497 | 755 |
| 3 | Form D | 7930 | 8201 | 8066 | 192 |
| 4 | Form H2 | 3068 | 2665 | 2867 | 285 |

ETP monoethanolamine salt Form D1 showed a relative solubility intermediate, that is lower than ETP monoethanolamine salt Form H (Entry 1).

ETP monoethanolamine salt Form H afforded a higher solubility than ETP monoethanolamine salt Form D1 (Entry 2).

Then, ETP monoethanolamine salt Form D1 has lower solubility in water respect to know ETP monoethanolamine salt Forms.

Thus, ETP monoethanolamine salt Form D1, affording one the most low solubility, is the most thermodynamic stable form according the stability study performed.

Example 8: Stability Study of Crystalline Eltrombopag Monoethanolamine Salt Form D1

Crystalline stability of Eltrombopag monoethanolamine salt Form D1 was studied under accelerated ICH guideline conditions (T=40° C./75±5% RH).

ETP monoethanolamine salt Form D1 obtained in the Example 1 was stored on a XRPD sample holder (10 mg) and exposed to ICH guideline accelerated stability conditions in the appropriate climate chamber (45±2° C.-75±5% RH). This sample was periodically analysed by XRPD in order to observe possible crystalline transformation or amorphization.

The crystalline Eltrombopag monoethanolamine salt Form D1 remaines stable for at least 2 months and said period could also be much longer. (The analysis has been carried out for 2 months).

The results show that during that study period, the crystalline ETP monoethanolamine salt Form D1 has remained stable, indeed polymorphic transition, hydrate formation or amorphization was not observed.

Moreover, a sample of ETP monoethanolamine salt Form D1 stored on a XRPD silicon holder was exposed in a climatic chamber. It is worth noting that these stability conditions are harsher than standard stability conditions due to the high surface of exposition of the solid stored on the XRPD silicon holder. The samples were periodically analysed by XRPD to observe possible crystalline transformation.

Finally, said that Eltrombopag monoethanolamine salt Form D1 has the best thermodynamic stability, as seen by the DSC and solubility study and confirmed by the stability study, in comparison with the known forms, and therefore is well suitable for pharmaceutical purposes. Moreover, ETP monoethanolamine salt Form D1 has the lowest hygroscopicity at 95% RH. Said features provide evident advantages in pharmaceutical compositions comprising ETP monoethanolamine salt Form D1.

The invention claimed is:

1. Crystalline Eltrombopag monoethanolamine salt Form D1 of formula (I):

(I)

having one of the following characteristic peaks of X-ray powder diffraction pattern expressed in 2-Theta values (2θ) at: 7.6, 11.6 and 16.5, each peak±0.2.

2. The crystalline Eltrombopag monoethanolamine salt Form D1 according to claim 1, having two or three of the following characteristic peaks of X-ray powder diffraction pattern expressed in 2-Theta values (2θ) at: 7.6, 11.6 and 16.5, each peak±0.2.

3. The crystalline Eltrombopag monoethanolamine salt Form D1 according to claim 1, having characteristic peaks of X-ray powder diffraction pattern expressed in 2-Theta values (2θ) at: 7.6, 10.5, 11.6, 16.5 and 19.9, each peak±0.2.

4. The crystalline Eltrombopag monoethanolamine salt Form D1 according to claim 1, having characteristic peaks of X-ray powder diffraction pattern expressed in 2-Theta values (2θ) at: 5.3, 7.6 and 8.5, each peak±0.2.

5. The crystalline Eltrombopag monoethanolamine salt Form D1 according to claim 1, having characteristic peaks of X-ray powder diffraction pattern expressed in 2-Theta values (2θ) at: 5.3, 7.6, 8.5, 11.6, 13.6 and 16.5, each peak±0.2.

6. The crystalline Eltrombopag monoethanolamine salt Form D1 according to claim 1, having DSC onset in the range of from 234° C. to 236° C. and/or DSC peak in the range of from 238° C. to 240° C.

7. A process for the preparation of the crystalline Eltrombopag monoethanolamine salt Form D1 of formula (I):

(I)

comprising:

a) providing a suspension of Eltrombopag in a solvent, b) heating the mixture of the step a) to give a solution, c) adding to the solution of the step b) an amount of ethanolamine to give a suspension of Eltrombopag monoethanolamine salt Form D1 of formula (I):

(I)

in a solvent, and d) isolating Eltrombopag monoethanolamine salt Form D1 from the suspension of the step c).

8. The process according to the claim 7, wherein the solvent of step a) is 1-pentanol or 1-butanol solvent.

9. The process according to claim 7, wherein the heating of step b) is carried out at reflux temperature.

10. The process according to claim 7, wherein the amount of ethanolamine of step c) is between 1.00 and 1.10 molar equivalent of ethanolamine.

11. A process for the preparation of the crystalline Eltrombopag monoethanolamine salt Form D1 of formula (I):

(I)

comprising:

A) heating solid Eltrombopag monoethanolamine salt Form H, having the characteristic peaks of X-ray powder diffraction pattern expressed in 2-Theta values (2θ) at: 4.9, 6.9, 15.1 and 23.0° 2θ±0.2°, at temperature in the range of from 200° C. to 210° C., B) maintaining at temperature of the step A) until the conversion of the product of step A) to Eltrombopag monoethanolamine salt Form D1 of formula (I), and C) cooling the product of step B).

12. The process according to the claim 11, wherein the heating of step A) is carried out at temperature in the range of from 200° C. to 205° C.

13. A pharmaceutical composition comprising a crystalline Eltrombopag monoethanolamine salt Form D1 according to claim 1, and one or more pharmaceutically acceptable excipients.

14. A method for the treatment of chronic immune thrombocytopenia, comprising administering the Crystalline Eltrombopag monoethanolamine salt Form D1 of claim 1 to a patient in need thereof.

* * * * *